United States Patent [19]

Tippetts et al.

[11] Patent Number: 4,771,007

[45] Date of Patent: Sep. 13, 1988

[54] ELECTRICAL CONDUCTIVITY DEVICE FOR DETECTING MASTITIS IN DAIRY COWS

[75] Inventors: Earl L. Tippetts; George B. Bersonnet, both of Cache County, Utah

[73] Assignee: Wescor, Inc., Logan, Utah

[21] Appl. No.: 43,169

[22] Filed: Apr. 27, 1987

Related U.S. Application Data

[63] Continuation of Ser. No. 475,942, Mar. 16, 1983, abandoned, which is a continuation-in-part of Ser. No. 359,282, Mar. 18, 1982, abandoned.

[51] Int. Cl.$^4$ .............................................. G01N 27/00
[52] U.S. Cl. ..................... 436/150; 119/14.01; 119/14.15; 204/409; 324/450; 422/68; 422/74
[58] Field of Search ................ 422/68, 74; 436/22, 436/23, 150, 151; 204/409; 119/14.01, 14.14, 14.15; 324/439, 442, 443, 450, 60.1 R, 60.1 C

[56] References Cited

U.S. PATENT DOCUMENTS

| | | |
|---|---|---|
| 2,593,878 | 4/1952 | Haines et al. |
| 3,004,071 | 10/1961 | Warner et al. |
| 3,158,444 | 11/1964 | Larson et al. |
| 3,173,969 | 3/1965 | Kapff |
| 3,516,876 | 6/1970 | Hauffe |
| 4,156,179 | 5/1979 | Stephen et al. |
| 4,158,809 | 6/1979 | Dellamano |
| 4,225,410 | 9/1980 | Pace |
| 4,309,660 | 1/1982 | Stephen |
| 4,325,028 | 4/1982 | Takahashi |
| 4,358,423 | 11/1982 | Nedetzky |

FOREIGN PATENT DOCUMENTS

| | | |
|---|---|---|
| 650199 | 2/1951 | United Kingdom |
| 743534 | 1/1956 | United Kingdom |
| B1194329 | 6/1970 | United Kingdom |
| 1438282 | 6/1976 | United Kingdom |

OTHER PUBLICATIONS

Mastizer-Electrical Conductivity Type Instrument for Diagnosing Mammary Disorders in Cows.

*Primary Examiner*—Michael S. Marcus
*Attorney, Agent, or Firm*—Mallinckrodt & Mallinckrodt

[57] ABSTRACT

An electrical conductivity testing device for detecting mastitis in dairy cows includes an inlet for receiving a sample of milk to be tested, a conductivity cell having a milk flow-through testing passage in flow communication with the inlet, and a milk discharge outlet in flow communication with the conductivity cell, so that a milk sample enters the inlet, flows through the conductivity cell, and flows out through the discharge outlet. The flow described may be continuous or may be discontinuous so that the sample is held in the conductivity cell at least during taking of the conductivity measurement. The conductivity cell is arranged so that it is completely filled with milk during the taking of conductivity measurements. Electrical circuitry is provided to produce an electrical signal proportional to the conductivity of the milk in the conductivity cell.

A preferred embodiment of the device takes conductivity measurements, individually and sequentially, of samples of milk from the four quarters of a cow's udder and produces electrical signals representing respective individual conductivity measurements on a scale of from 0 to 9 by electrical comparison of such conductivity measurements with a reference value, preferably by means of a bridge amplifier circuit, and exhibits respective digits representative of such measurements, preferably side-by-side, on a readout screen provided as a part of the instrument.

14 Claims, 3 Drawing Sheets

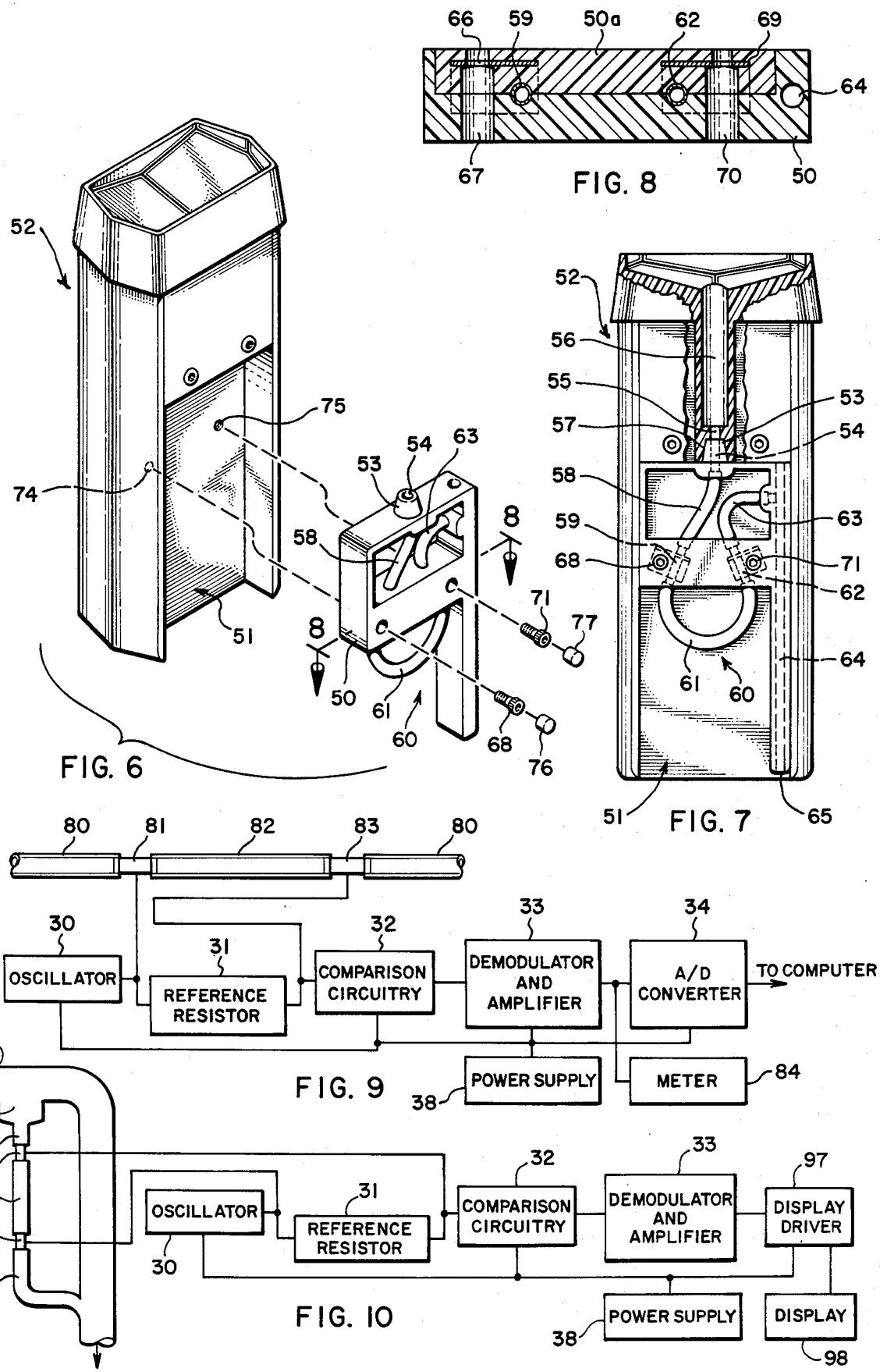

ELECTRICAL CONDUCTIVITY DEVICE FOR DETECTING MASTITIS IN DAIRY COWS

RELATED APPLICATIONS

This application is a continuation of application Ser. No. 475,942 file Mar. 16, 1983, abandoned, which was a continuation-in-part of application Ser. No. 359,282 filed Mar. 18, 1982, abandoned.

BACKGROUND OF THE INVENTION

1. Field:

This invention is in the general field of mastitis detecting devices for use in the dairy industry and is particularly concerned with devices of this type that test electrical conductivity of milk secretions of the mammary glands of dairy cows.

2. State of the Art:

Various ways of testing dairy cows for the disease known as mastitis, which infects the mammary glands of a great many of the dairy cows being milked throughout the world, have been developed in the past. None of these have been entirely satisfactory. Viscosity testing of milk from each of the four quarters of the udder of a dairy cow is commonly used in the U.S.

Testing electrical conductivity of the milk has been tried experimentally in the U.S. and has been used in New Zealand. Infected quarters of an udder produce milk lower in lactose and higher in sodium chloride than quarters of an udder that are not infected, and electrical conductivity of such milk is not the same as that from non-infected quarters. Ordinarily, not all quarters of a dairy cow's udder are infected or infected to the same degree, so that comparing the electrical conductivity of milk taken sequentially from the four quarters provides a reasonably reliable indication of mastitis infection.

A conductivity test instrument which has achieved significant commercial success in New Zealand, where it was developed, is described in an article entitled "Method of Mastitis Detection Including the Rolling Ball Viscometer and Electrical Conductivity Meter" by Graham F. Doire appearing on pages 25-34 of the Proceedings of the 19th Annual Meeting of the National Mastitis Council Inc. held at Louisville, Ky., on Feb. 18-20, 1980. It provides for measuring conductivity of milk from the four quarters of a dairy cow's udder individually and in sequence and includes a switching system controlling the energizing of a green and red light, individually or together, to indicate relatively low, relatively high, and intermediate conductivity measurements, respectively. The four readings are recorded by an observer and compared to establish a positive or negative condition for each quarter.

Although this New Zealand device has the advantages of being relatively inexpensive and easily operated by a dairyman at cowside, with more easily and more quickly interpretable results than had been possible theretofore, it requires a second person to be present to record the results of each quarter testing and does not provide adequately for differences in herd type, particular stages of lactation, or individual cow chemistry.

Further, in use, milk is introduced into a closed-bottom conductivity cell, the measurement taken, and then the cell turned upsidedown to empty the milk before another sample of milk is placed in the cell for testing. It has been found with such a device that milk remains on the sides of the cell after the sample is poured out, so that, after several readings have been taken, the samples become contaminated and the cell has to be cleaned before further use. Ideally, the cell should be cleaned after every use.

In the U.S., where testing has been done regarding the relationship between conductivity readings and the presence of mastitis, the tests have all been experimental using laboratory bench-type conductivity meters. Again, such meters have closed-bottom conductivity cells to hold the samples of milk being tested or prong-like conductivity cells which are inserted into closed-bottom containers holding the samples, and in both cases, the cells and containers must be washed out each time a test is made.

SUMMARY OF THE PRESENT INVENTION

According to the invention, an electrical conductivity testing device for detecting mastitis in dairy cows includes means, such as a funnel-like receptacle, for receiving a sample of milk to be tested, an electrical conductivity cell having a milk flow-through testing passage in flow communication with the sample receiving means, and milk discharge means in flow communication with the conductivity cell so that a sample enters the receiving means, flows through the conductivity cell and flows out through the discharge means. A loop formation in the testing passage, is provided to ensure that the conductivity cell is completely full of milk when testing electrical conductivity and electrical circuitry is connected to the conductivity cell for powering such cell and generating an electrical signal representative of the conductivity of the milk in the cell.

The device of the invention is constructed for use as a hand-held instrument by a dairy farmer at cowside.

In one preferred embodiment of the device, conductivity measurements are made of the four quarters of a cow's udder, individually and sequentially, with a hand-held instrument by sequentially passing respective samples of milk through a flow-through conductivity cell of the instrument, and electrical signals representing respective individual conductivity measurements are obtained on a scale of from 0 to 9 by electrical comparison with a reference value, preferably by means of a bridge amplifier circuit that senses electrical impedance deviations from a known reference impedance, and by exhibiting the measurements on a readout screen provided as a part of the instrument.

The individual measurement values are put into display form on the readout screen by demodulating and amplifying the respective electrical signals from the bridge circuit, by applying them to an analog to digital converter, and by feeding the output of such converter to a display driver. Display digit control is preferably accomplished manually by means of individual electrical switches corresponding to the respective quarters of the udder. Operation of the switches causes a final comparative display of four digits representing the four quarters of the udder being tested.

Thus, this embodiment of the invention provides for a simultaneous, comparative display of conductivity measurements of all four quarters of a cow's udder and responds quickly to procedures easily carried out by a single operator working at cowside. The device can be manufactured and sold at a price well within the ability of individual diarymen working their own small dairy farms.

THE DRAWINGS

In the accompanying drawings, which illustrate an embodiment of the device constituting the best mode presently contemplated of carrying out the invention in actual practice:

FIG. 1 is a front elevational view of the device as it is held by a dairy farmer for testing and for viewing the readout screen;

FIG. 2, a top plan view showing where the milk samples are deposited for testing purposes;

FIG. 3, a rear elevational view, with portions of the housing broken away to show otherwise hidden parts;

FIG. 4, a block diagram showing how electrical and electronic equipment are interconnected into operative test and display circuitry;

FIG. 5, a detailed wiring diagram and schematic of the system as a whole;

FIG. 6, an exploded view of a second embodiment of the device of FIG. 1 showing how the conductivity cell may be mounted as a removable insert for ease of replacement;

FIG. 7, a rear elevation of the device of FIG. 6 with insert in place and part of the casing broken away to show milk receptacle and the flow path of successive milk samples; and FIG. 8, a horizontal section taken on the line 8—8 of FIG. 6 showing the construction of the electrodes.

DETAILED DESCRIPTION OF ILLUSTRATED EMBODIMENTS

Figure 2:
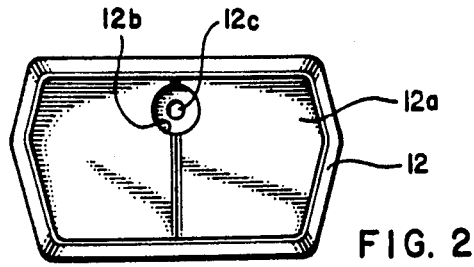
Figure 1:
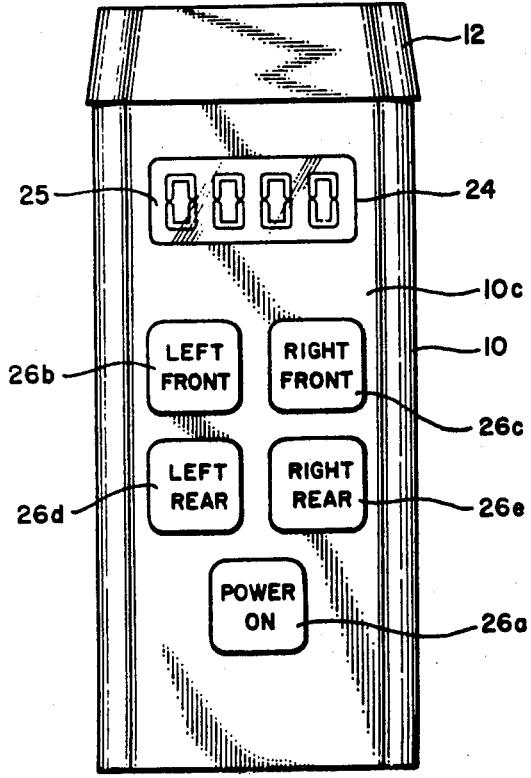
Figure 3:
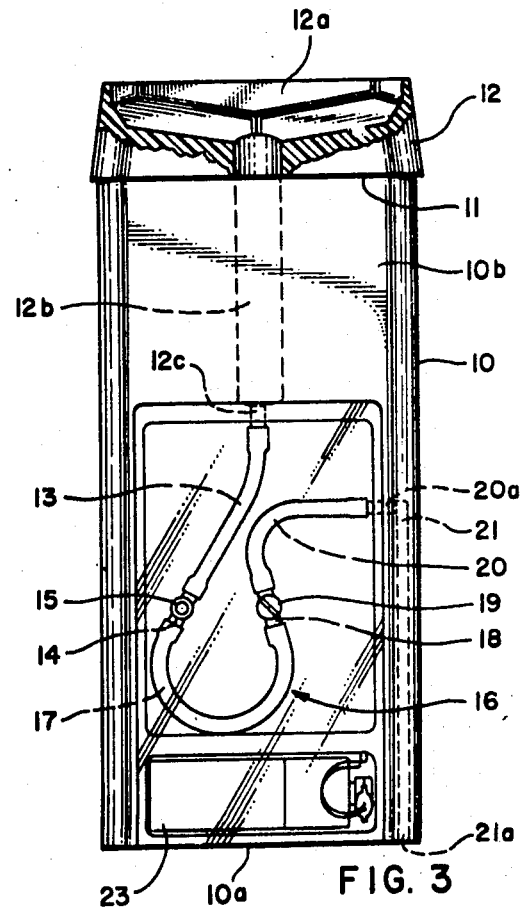

In the embodiment illustrated in FIGS. 1–3, the electrical components are compactly housed within a casing 10, FIGS. 1–3, adapted to be held by a hand of a dairyman located by the side of a dairy cow and ready to withdraw milk from the four quarters of the cow's udder sequentially.

Casing 10 is preferably injection-molded to shape from a suitable plastic material, such as acrylic butadiene styrene, better known as A.B.S. Its top is open as at 11, FIG. 3, and is formed for receiving and retaining a cap 12, which is also preferably injection molded to shape from a suitable plastic material such as the same acrylic butadiene styrene as the casing 10 on which it fits. Cap 12 is of funnel formation, having an open top portion 12a, FIG. 2, funneling into a depending discharge spout 12b, FIG. 3, serving as a milk reservoir which terminates in a nipple type of connection fitting 12c of considerably reduced diameter. Reservoir 12b provides a receiving means for the sample of milk to be tested.

Attached to nipple 12c is one end of a length 13 of flexible tubing, which serves as an air entrapment device. Its other end is attached to an end of a relatively short length 14 of stainless steel tubing passing through an electrical binding post 15, so as to become one electrode of an electrical conductivity measurement cell identified in general as 16. Such cell 16 is completed by connection of another length 17 of flexible tubing to an end of a second, relatively short length 18 of stainless steel tubing which passes through a second electrical binding post 19 to become the second electrode of such conductivity measurement cell 16.

The other end of stainless steel tubing 18 is connected to another length 20 of flexible tubing, whose other end is attached to a stainless steel nipple 20a connected to a rigid, discharge tube 21, which is preferably molded integrally with casing 10 and has an open end 21a communicating with the atmosphere through the otherwise closed bottom 10a of casing 10, comprising discharge means for the device.

As a matter of convenience in the use of the device, the rear wall 10b of casing 10 is windowed, as at 22, so as to expose to view from the exterior of the casing conductivity measurement cell 16 and a nine volt, dry cell battery 23, which powers the unit.

The front wall 10c, FIG. 1, of casing 10 is windowed at 24 to expose a readout screen 25 to view from the exterior of the casing. In the present embodiment, five manually operated, switch push buttons 26 are mounted in front casing wall 10c below readout window 24.

Readout screen 25 is part of an electrical, digital, display device of standard type, such as a Fairchild LTB1042RSX, providing for, in this instance, side-by-side display of four digits, each being one of a series of possible digits from zero to nine as automatically selected according to respective results of sequential tests of milk drawn by the operator from the four quarters of a dairy cow's udder. Thus, the device of the invention provides a comparative readout of the test results on all four quarters of the udder.

In using the device, milk is squirted directly from the teat concerned into the funnel top 12a of cap 12. One or two squirts is sufficient. The milk funnels down into reservoir 12b and more slowly from there into and through stainless steel tubing 14, non-conductive, flexible tubing 17, and stainless steel tubing 18 constituting conductively measurement cell 16. The conductivity measurement is obtained almost instantaneously as the milk sample flows through on its way to discharge tube 21.

The tubes leading to and from conductivity cell 16, as well as the cell itself, are arranged in loop fashion, with the outlet of the loop below the inlet thereof, as shown, in FIG. 'so that a milk sample will enter the cell and flow therethrough until the inflow milk level in tube 13 is at the level of the top of discharge tube 21 and, thus, fills the tubes and cell therebetween. At this point, the sample remains in the conductivity cell 16 until either a new sample is introduced into the cell to force out and replace the previous sample therein, or until the device is tipped in such manner to allow the sample to flow out. In this way, it is easy for a farmer to introduce a milk sample into the device and obtain a reading at his own speed without having to take a reading at the exact time the milk flows through the cell and possibly miss a reading because his timing is not fast enough.

Given equilibrium for each sample, with the sample milk level in tube 13 equal to the longer level of the discharge tube 21, each subsequent milk sample will force an air bubble from the entrance portion of tube 13 into the conductivity cell in advance of such sample, so as to purge the system of the immediately preceding milk sample.

It has been found that the flow-through system described is extremely in completely flushing one sample from the system as the next sample is introduced, so that there is substantially no detectable mixing of samples or contamination of the sample as it flows into, through, and out of the cell. This avoids the necessity of cleaning the cell after every use, or after every set of several uses, to avoid mixing and contamination from sample to sample as is the case in cup-type conductivity cells if now washed thoroughly.

It is important in order to obtain accurate conductivity readings that the same volume of milk be in the cell each time a reading is taken. For this reason, it is important that the cell be completely full of milk for each conductivity reading taken. In the embodiment of the device shown in FIGS. 1-3, this is accomplished by making reservoir 12b of relatively large capacity in comparison with substantially the combined capacities of conductivity cell 16, nipple 12c, and tube 13 leading from reservoir 12c to conductivity cell 16. Thus, conductivity cell 16 has a volume of about 2 ml while a squirt or two of milk into reservoir 12c provides significantly more than that volume and more than encompasses the opening into nipple 12c to insure that milk substantially without air bubbles flows into tubing 13 and into cell 16.

Figure 4:
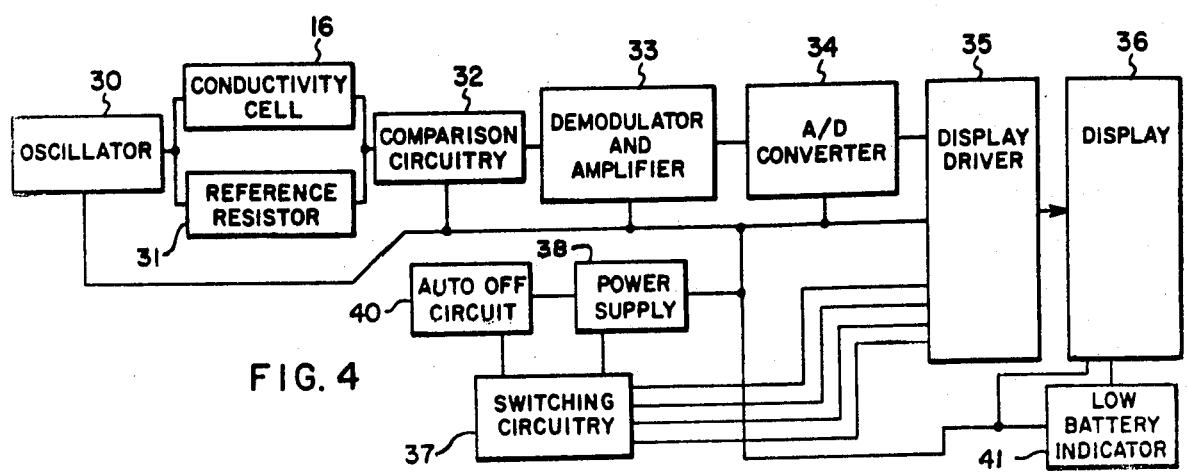

The electrical circuitry presently contemplated as best for this embodiment of the invention is shown generally in block form in FIG. 4. An oscillator 30 supplies an A.C. signal to the conductivity cell 16 of the unit and to a reference resistor 31. The signal passing through the reference resistor is compared to the signal passing through the conductivity cell in comparison circuitry 32, and the output of the comparison circuitry (an A.C. signal proportional to the difference in resistance between the conductivity cell and the reference resistor) is converted to a D.C. analog-difference signal and amplified by demodulator and amplifier 33. The D.C. signal from demodulator and amplifier 33 is fed to an analog to digital converter 34, where such analog-difference signal is converted to a digital signal which is sent to a display driver 35 operating a digital display device 36 adapted to display an appropriate digit in a selected part of readout screen 25.

Figure 5:
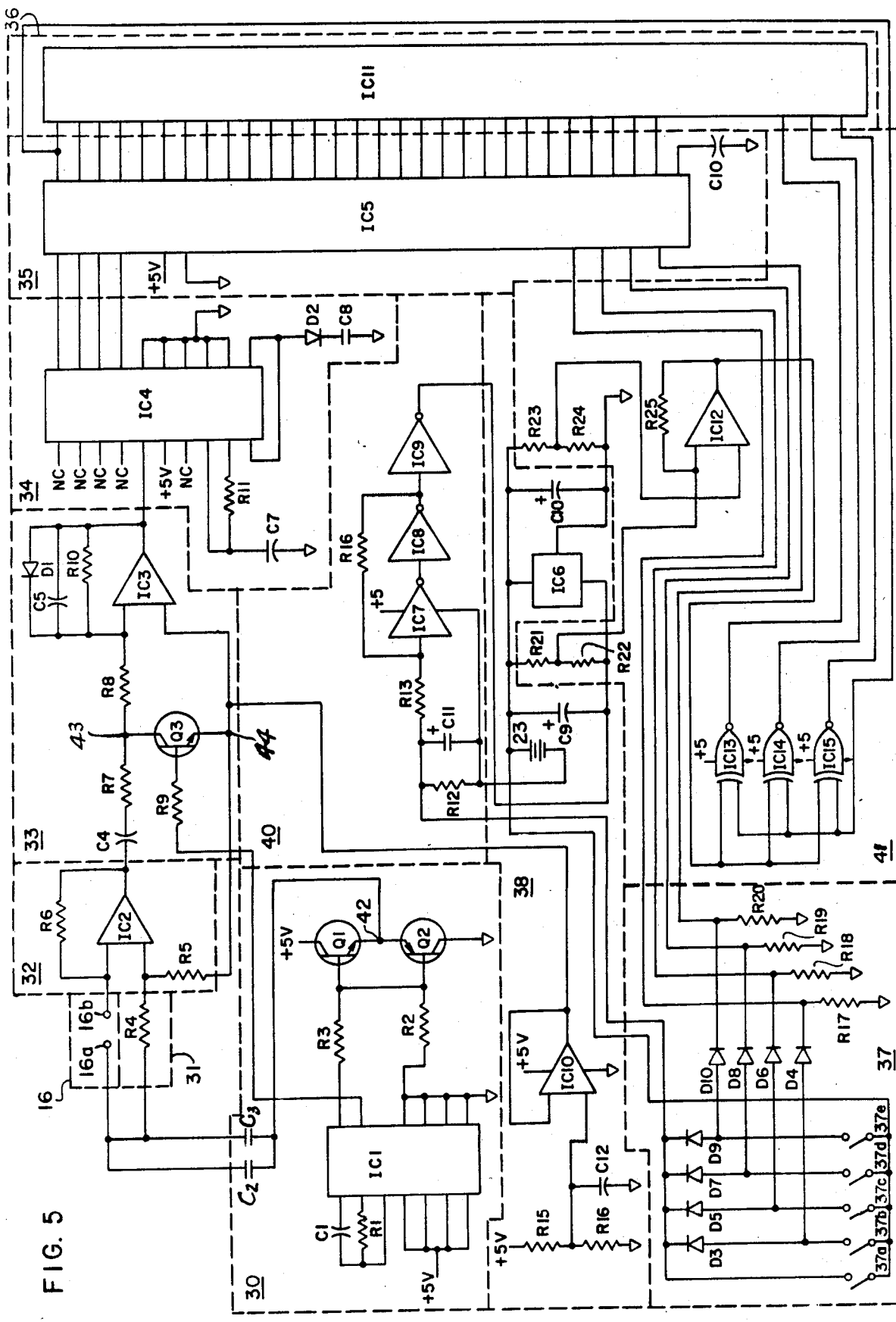

Switching circuitry 37, FIG. 5, contains five switches, an "on" switch 37a operated by the appropriately-designated push button 26a, and four separate switches 37b-37e operated, respectively, by push buttons 26b through 26e designated for the respective four quarters of a cow's udder.

In operation, "on" switch 37a is first actuated to supply power to the various components of the circuitry from power supply 38 which includes battery 23. Power supply 38 is connected to all circuitry components, as indicated. After the power is turned on, each of the four quarters are tested in turn by sequentially passing milk therefrom through the conductivity cell and by pushing corresponding test buttons 26b through 26e.

An automatic off-circuit 40 is provided to turn off the power supply after a preset time period, so that the unit is not accidentally left on when not in use. This prevents the battery from becoming unnecessarily discharged. This auto-off circuit is preferably set to turn off the power supply twenty to thirty seconds after the "on" switch or any one of the test switches is closed. A low battery indicator circuit 41 is preferably provided to give an indication when the battery becomes discharged and should be replaced.

Variously constructed circuits could be used for each of the blocks described above. However, the circuitry shown in FIG. 5 is the best presently contemplated for use in the device. The individual circuits corresponding to the individual blocks in the diagram of FIG. 4 are marked off by broken lines and correspondingly designated.

As shown, oscillator 30 comprises an astable, multivibrator, integrated circuit IC1, such as a CD4047BE manufactured by RCA. The output of IC1 is a square wave, the frequency of which is set by capacitor C1 and resistor R1. The square wave output of IC1 is connected through resistors R2 and R3 to the bases of transistors Q1 and Q2. Resistors R2 and R3 reduce the voltage from IC1. The square wave from IC1 alternately turns on transistors Q1 and Q2, thereby giving a square wave output at terminal 42 between the transistors which is reduced in amplitude to about 2.8 volts rather than the 5 volt amplitude from IC1. The purpose of transistors Q1 and Q2 is to reduce the source impedance of the oscillator circuit. The reduction in the voltage of the square wave output from five volts to 2.8 volts is to lower the output below the common mode voltage of the amplifier IC2 in the next stage. This prevents overloading of that amplifier.

The square wave signal from terminal 42 is connected through capacitor C2 to one electrode 16a of conductivity 16. The square wave signal is also connected through capacitor C3 to resistor R4, which is the reference resistor heretofore designated 31. Capacitors C2 and C3 block any D.C. component of the square wave signal from the oscillator.

The second electrode 16b of conductivity cell 16 is connected to one input terminal of a differential operational amplifier IC2, such as an ICL 7641 made by Intersil, in comparison circuitry 32. Thus, the signal passing through the milk sample in the conductivity cell is fed to one input of IC2. The signal passing through reference resistor R4 is fed to the other input of IC2. Conductivity cell 16, together with resistor R4, additional resistors R5 and R6, and integrated circuit IC2, form a bridge amplifier network which has two fewer components than a conventional bridge amplifier network and has better impedance characteristics so that bridge loading due to amplifier input resistance is not a factor. The A.C. transfer function of this bridge amplifier network is shown by conventional operational amplifier theory as:

$$\frac{Eo}{Ein} = \frac{Rf}{RC} \frac{(R4 - RC)}{(R4 + Rf)}$$

where R5 and R6=Rf, and RC is the resistance of the conductivity cell.

With the resistance of resistor R5 equal to that of resistor R6, resistor R4 establishes a known reference value for comparison with the resistance measured by conductivity cell 16. Thus, the output of IC2 is a square wave, with amplitude proportional to the difference in resistance between the conductivity cell and reference resistance R4.

The output of IC2 is demodulated and amplified in circuit 33. The signal from IC2 passes through capacitor C4 and resistors R7 and R8 and is connected to one input terminal of differential operational amplifier IC3, which is similar to IC2. Transistor Q3 is connected, at 43, between the signal line connecting resistor R7 with R8 and a line 44 carrying a reference voltage of 2.5 volts from the power supply of 38, which is one-half the standard five volt output of such power supply, as explained below. This reference voltage is also connected to the other input terminal IC3. The base of transistor Q3 is connected, through current-limiting resistor R9, to an output of multivibrator IC1, which produces a high, i.e. five volt signal, during the high, i.e. five volt cycle, of the square wave. This high signal turns on transistor Q3 during half a cycle of the square wave and, when the transistor is "on", clamps point 43 to substantially the reference voltage of 2.5 volts. This puts a D.C. component in the square wave signal from IC2 after passing through C4. Capacitor C4 blocks this D.C. component from the comparison circuitry.

Integrated circuit IC3, in conjunction with feedback resistor R10 and capacitor C5, act to filter out the A.C. component of the signal on the input of IC3 and provides output from IC3 that is a D.C. signal biased to 2.5 volts and proportional to the difference in resistance between the resistance of the conductivity cell and reference resistor R4. Diode D1 is provided to clamp the output of IC3 to a maximum value, so that no number greater than nine will be indicated by the display.

The output of IC3 is connected to the analog input of an analog to digital converter IC4 (box 34), such as an ADC0804 made by National Semiconductor. Since the input to IC4 is limited as described, so that only outputs indicating numbers between zero and nine are obtained from IC4, the outputs of IC4 representing the four most significant bits are used. They are fed into display driver IC5 (box 35), such as a DF411CJ made by Siliconix. R11 and C7, as connected to IC4, set the timing of the internal clock, and D2 and C8, also connected to IC4, are provided to insure proper start-up of the internal oscillator.

As previously indicated, power is supplied to the circuitry by a standard nine volt battery 23. The positive terminal of the battery is connected to the ground input terminal of a five volt voltage regulator IC6, such as an LM 320 MP-5.0 made by National Semiconductor. This ground terminal is used as the positive, five volt terminal for the circuitry. The negative terminal of the battery 23 is connected through the automatic shut-off circuitry 40 to the input terminal of regulator IC6. The regulated output terminal from IC6 is used as the ground terminal for the circuitry. Capacitor C9 is a filter capacitor for the input to IC6, while capacitor C10 is a filter capacitor for the output from IC6.

The positive terminal of battery 23 is also connected to one side of push button switches 37a though 37e in switching circuit 37. Switch 37a is the power "on" switch controlled by the lowermost push button 26a. When push button 26a is depressed, switch 37a is closed to thereby connect the positive five volt supply to the parallel combination of resistor R12 and capacitor C11, and such combination across the terminals of the battery. With switch 37a closed, capacitor C11 is charged to nine volts. This positive voltage is connected to inverter IC7 through resistor R13. When push button 26a is released, switch 37a opens and capacitor C11 discharges through resistors R12 and R13. The time constant for the circuit is set so that capacitor C11 remains sufficiently charged to provide a positive input to IC7 for a period of between twenty and thirty seconds.

With this positive voltage on the input to inverter IC7, the signal is inverted. It is inverted again by IC8 and again by IC9, so that the output of inverter IC9 is approximately a negative four volts. Resistor R14 is a feedback resistor supplying positive feedback to IC7 to cause the inverters to switch more quickly.

The minus four volt signal from IC9 is sent to the input of voltage regulator IC6 in power supply circuit 38 and serves to energize the power supply. When capacitor C11 discharges to the extent that it no longer provides a positive input to IC7, the output of IC9 goes to plus five volts which, in effect, connects the input of IC6 to the plus five volts line which is also the ground connection for IC6. This results in zero voltage potential across IC6 so that no power is supplied to the circuit.

As part of power supply circuit 38, resistors R15 and R16 are connected between plus five volts and ground as a voltage divider. The voltage between resistors R15 and R16 is connected to one input of differential operational amplifier IC10, similar to IC2. The output of IC10 is connected back to its other input as feedback. A filter capacitor C12 is connected in parallel with R16. The output voltage of IC10 is one-half the supply voltage, i.e. 2.5 volts. This is used by comparison circuitry 32 and by demodulator and amplifier circuitry 33 as explained above.

Switch 37b is the switch for the left front quarter of the udder. When 37b is closed, the positive voltage is again connected so as to charge capacitor C11 and thereby again start the timing cycle of power supply 38. The positive voltage is connected to C11 through diode D3, which prevents any back flow of current from C11 when 37b is open. With 37b closed, positive voltage is also supplied through diode D4 across resistor R17 to display driver IC5 (box 35). This input to the display driver causes the digital number input to the driver from analog to digital converter 34 to be displayed in the extreme left position of the readout screen 25 of display IC11 (box 36). This display will now remain, even when 37b is opened. Display IC11 is preferably a liquid crystal display, such as a Fairchild LTB1042RSX.

Switch 37c is the switch for the right front quarter of the udder. When 37c is closed, a positive voltage is supplied through a diode D5 to again charge capacitor C11, to keep the circuit energized for an additional time period. The positive voltage is also supplied through a diode D6 across a resistor R18 to the terminal of display driver IC5, which causes the number then on the input to the display driver to be displayed in the second from the left position in the display.

Switch 37d represents the left rear quarter of the udder, and when closed, similarly charges capacitor C11 through a diode D7 and supplies a positive voltage through a diode D8 across a resistor R19 to display driver IC5. This voltage on IC5 causes the number then on the input of IC5 to be displayed in the third from left position of the readout screen 25 of display IC11, i.e. box 36.

Switch 37e represents the right rear quarter of the udder, and, when closed, both charges capacitor C11 through a diode D9 and supplies a positive voltage through a diode D10 across a resistor R20 to display driver IC5. This voltage on IC5 causes the number then on the input to IC5 to be displayed in the fourth position from the left of the readout screen 25 of display IC11.

Thus, if "on" switch 37a is activated by manually pressing its push button 26a and milk from the left front quarter of the udder is squirted into the device and flows into conductivity cell 16 thereof, analog to digital converter IC4(34) will supply a signal to the four parallel lines connecting IC4 with IC5 (35) representative of a number between zero and nine which is proportional to the difference in resistance between reference resistor 31 and conductivity cell 16. If switch 37b is now closed by pressing its push button 26b, that number will appear in the extreme left position of the readout screen 25 and will remain displayed as long as the power remains on. Push button 26b should be pressed only momentarily and then released to open switch 37b again and to hold the number representative of the conductivity of the milk from the left front quarter in the display. It should be noted that push button 26b must be pushed while the milk sample to be measured is in the conductivity cell 16.

With switch 37b open, milk from the right front quarter is squirted into the device. Conductivity of this new sample will be measured and displayed in the second from the left position of readout screen 25 when switch 37c is closed by pressing its push button 26c.

If the same procedure is followed for samples of milk from the left rear quarter and right rear quarter of the udder and switches 37d and 37e are closed, respectively, the display on readout screen 25 will show four digits side-by-side, each between zero and nine representing the conductivity measurements for the milk samples from each of the four quarters of the udder. With these side-by-side measurements, it is easy to determine which, if any, of such quarters are infected with mastitis.

As indicated above, milk from a quarter of the udder which is infected with mastitis will be higher in sodium chloride content and lower in lactose content than milk from non-infected quarters. Thus, milk from infected quarters will have a higher conductivity than milk from non-infected quarters. Although with the same herd type differences in particular stages of lactation and individual cow chemistry affect the conductivity of normal milk, it does so only to limited extents. Thus, there is a point at which conductivity above a certain maximum value for a particular herd type indicates mastitis infection. It is preferred that the value of the reference resistor be chosen so that the sensitivity of the comparison circuitry and demodulator and amplifier circuitry be such that any reading on the display of the instrument of "5" or over indicates a conductivity above this maximum and indicates an infected quarter. Thus, any reading obtained for a quarter which is "5" or above indicates mastitis infection. If readings for all quarters are "5" or above, all quarters are infected.

Mastitis can be present even when conductivity of the milk does not reach the maximum level. In such cases, however, it is very unlikely that all quarters of the udder will be infected. Also, in such cases, the milk from the infected quarter or quarters will be higher in conductivity that milk from the other quarters. Variations of one or two counts in the output of the device is normal between milk from different quarters, but differences of three counts or more indicates that the quarters with the higher counts are infected.

After measurement of conductivity of all four quarters is complete so that four digits representing the conductivity measurements are side-by-side on the display, the user of the instrument can easily determine the lowest reading and differences in readings and determine if mastitis infection is present and, if so, in which quarter or quarters of the udder.

It is preferred that the circuitry include an indicator, see box 41, FIGS. 4 and 5, to show when the battery becomes low and should be replaced. For this purpose, resistors R21 and R22 form a voltage divider between the five volt supply from power supply 38 and the minus four volt output of IC9, this being substantially across the full nine volts of the battery. Resistors R23 and R24 form a voltage divider for the five volt regulated output from IC6. The divided voltage between resistors R21 and R22 is supplied to one input terminal of a differential operational amplifier IC12 similar to IC2, while the divided voltage from between resistors R23 and R24 is supplied to the other input terminal of IC12.

As the battery discharges, the voltage across resistors R21 and R22 will decrease, while the regulated five volt supply will remain substantially constant. By adjusting the resistance values of the two dividers, the voltages on the two inputs to IC12 can be adjusted so that, as the battery discharges to a certain value, the difference in voltage on the two inputs to IC12 will have changed sufficiently to cause an output signal from IC12. Resistor R25 is a feedback resistor.

The output of IC12 is connected to one input of exclusive "or" gates IC13, IC14, and IC15, all of which may be included on a single chip, such as a CDb 4030 made by RCA. The other input terminal of "or" gates IC13, IC14 and IC15 are connected to an oscillator output of display driver IC5. As long as the output of IC12 is low, i.e. zero volts, the output of the "or" gates IC13, IC14, and IC15 are in phase with the oscillator and no display is caused. When the battery becomes low, IC12 produces a high, i.e. plus five volt, output causing the output of each of IC13, IC14 and IC15 to be out of phase with the oscillator. This out-of-phase input to the display IC11 causes three decimal points to be displayed in the three righthand positions of the display on readout screen 25. These three decimal points provide a visual indication of a low battery.

It should be realized that some of the integrated circuits indicated, such as the differential operational amplifiers, the inverters, and the exclusive "or" gates, while being independent devices, may be included on a single chip. For example, the exclusive "or" gates IC13, IC14, and IC15 are all supplied on a single chip as identified, which includes an additional "or" gate not used. The operational amplifiers are also supplied on a single chip as identified, as are the inverters.

While, as indicated above, there are normally relatively small differences between conductivity values of milk from the four different quarter of a cow and from cow to cow of the same herd type, there are substantial differences in the normal conductivity values of milk from different herd types and in the conductivity value that is generally considered to be the threshold value indicative of the presence of mastitis. For example, a conductivity reading of 6118 u seimens is generally considered the threshold value to indicate the presence of mastitis in Jersey cows, while a value of 7157 u seimens is considered the threshold value for Holsteins.

As explained above, it is preferred that the instrument be calibrated so that a "5" indicates the threshold conductivity value and, thus, so that a "5" or above indicates an infected cow. It is undesirable to have to recalibrate the electronics each time the device is used with a different herd, or even to have to provide different instruments having different electronics calibrated to a particular type of cow.

It has been found that a change in calibration can most easily be made by changing the conductivity cell. For a conductivity cell of the type shown, the reading varies depending upon the length of the cell (distance between the electrodes) and the cross-sectional area of the cell. With a constant cross-sectional area, varying the length of the cell will give different readings with the same reference bridge. The length required is given by the following formula:

$$l = \frac{CAR}{10^6}$$

where l=length, C=conductivity, A=cross-sectional area, and R=resistance.

The resistance is the effective measured resistance of the conductivity cell necessary to give a reading of "5" on the display. This value will vary and is dependent upon the resistance of the reference resistor 31 and may vary with other specific circuit values.

In the circuitry shown, with the reference resistor having a resistance of about 10k, it has been found that a conductivity cell resistance of about 11,787 ohms is needed to give a reading of "5". Thus, the length of the conductivity cell can be determined for any particular threshold value of conductance. Using a tube size of 0.125" inside diameter and the threshold value of 7157 u seimens for Holstein cows, the length of the conductivity cell must be 6.67 cm for the threshold value to produce a reading of "5". With the same electronics and the same size tubing, the cell must be 5.7 cm long to give a reading of "5" for the threshold conductivity value of 6118 u seimen for Jersey cows.

FIGS. 6, 7, and 8 show an embodiment of the invention in which the conductivity cell is mounted so that it can be easily replaced with cells calibrated for different herd types.

In this embodiment, a removable frame 50 is received within recess 51 of a casing 52 that is similar to casing 10 of FIGS. 1-3. A resiliant conical seal member 53 is positioned about a nipple-type connection fitting 54, one end of which is received by passageway 35 in the bottom of a milk reservoir 56 that is similar to reservoir 12b of FIGS. 1-3. Conical seal member 53 is received by a similarly shaped receiving opening 57, so that a seal is formed and all milk from reservoir 56 is directed into nipple 54.

Attached to the other end of nipple 54 where it passes through frame 50 is one end of a length 58 of flexible tubing, which leads to the conductivity cell and also serves as an air entrapment device. Its other end is attached to an end of a relatively short length 59 of stainless steel tubing which serves as one electrode of an electrical conductivity measurement cell identified generally as 60. Such cell is completed by connection of another length 61 of flexible tubing to an end of a second, relatively short length 62 of stainless steel tubing which serves as the second electrode of the conductivity measurement cell 60. The other end of stainless steel tubing 62 is connected to another length 63 of flexible tubing, whose other end is attached to discharge passage 64 which is preferably molded integrally with frame 50 and has an open end 65 communicating with the atmosphere through the bottom of frame 50.

Stainless steel tubing sections 59 and 62 are encased in frame 50 by means of insert piece 50a which is glued into place on frame 50. A copper plate 66 is soldered to tubing 59 and extends about screw hole 67, so that a screw 68 passing through such hole will make electrical contact with plate 66 and, in turn, with tube section 59. A similar copper plate 69 is soldered to tubing section 62 and extends about screw hole 70 to make electrical contact with a screw 71 passing therethrough.

Frame 50, with conductivity cell 60 secured therein is inserted into casing 52 by inserting nipple 54 and seal 53 into receiving holes 55 and 57, respectively, and placing the frame against casing 52 in recess 51. Screws 68 and 71 are inserted through holes 67 and 70, respectively, and into receiving holes 74 and 75 in casing 52. Binding posts are provided within holes 74 and 75 in the casing, so that screws 68 and 71 serve to electrically connect the respective electrodes of the conductivity cell to the circuitry housed in casing 52. The circuitry is the same as that already described. Rubber stoppers 76 and 77 fit into holes 67 and 70 to seal them against build-up of dirt or other debris. It should also be noted that in the embodiment of FIGS. 6-8, the battery (not shown) has been moved from its position as shown in FIGS. 1-3 to a position inside casing 52. This provides room for insertion of frame 50 with its conductivity cell 60, and protects the battery from milk which may be spilled on the unit.

While it is preferred to measure each quarter separately, so the readings for each quarter may be compared, in some instances, particularly where the device is used for evaluating milk in a laboratory rather than at cow side, a single reading may be taken and determination made of the presence of mastitis based solely on the value of the reading. Further, while an LCD readout is described, a digital meter or panel meter or some other indicator, such as an LCD bar graph indicator, may be used. With a bar graph indicator, the analog output of the demodulator and amplifier 33 is fed directly to a display device, such as an LM 3914 made by National Semiconductor, which is connected to and drives a bar graph display, such as an MV 57164 made by General Instrument.

The electrodes for the conductivity cells have been described as stainless steel, but various other conductive materials may be used. However, stainless steel is preferred, since it is approved for use in dairy equipment and does not affect the milk.

Whereas this invention is here illustrated and described with specific reference to embodiments thereof presently contemplated as the best mode of carrying out such invention in actual practice, it is to be understood that various changes may be made in adapting the invention to other embodiments without departing from the broader inventive concepts disclosed herein and comprehended by the claims that follow.

We claim:

1. A hand-held, electrical, conductivity testing device for detecting mastitis in dairy cows, comprising reservoir means for receiving spaced, successive samples of milk as squirted directly from a teat of a cow to be tested and of a volume to be at least partially filled by a single squirt of milk; two lengths of electrically conductive tubing; a length of electrically non-conductive tubing joining the lengths of electrically conductive tubing to form an electrical conductivity cell wherein the lengths of electrically conductive tubing form the electrodes of the cell; tubing means in combination with the electrical conductivity cell forming a milk-flow-through testing passage, said electrical conductivity cell being included as an integral part of said passage intermediate its ends, said passage being smaller in cross-section than said reservoir means and connected in fluid-flow communication with said reservoir means to form an inlet to said passage, so that milk will flow from said reservoir means into and through said passage, said passage being configured as a loop having its inlet and an outlet above the conductivity testing cell when the device is held in normal testing position, milk to be tested entering the conductivity cell from said reservoir means and remaining there until forced out by the next sample or until otherwise emptied, the said outlet of said passage being located below the said inlet thereof, so that, when a sample of milk reaches equilibrium in said passage, no milk is present in the reservoir or passage inlet, whereby, when a successive sample of milk is received in said reservoir means, an air bubble will be formed in the upper part of said passage between the sample at equilibrium and the successive sample, and the inside diameter of said testing passage being small enough to be effective to maintain any bubbles of air trapped between successive samples as bubbles between such samples and to maintain such bubbles between said samples as the samples flow through the passage to thereby flush the preceeding sample from the conductivity cell; milk discharge means connected in fluid-flow communication with the outlet end of said passage to allow the sample to flow from said passage; and electrical means electrically connected to the respective electrodes of the conductivity cell for generating an electrical signal representative of the conductivity of the sample of milk in the cell at any given time.

2. An electrical conductivity testing device according to claim 1, wherein the device is adapted to sequentially measure the conductivity of samples of milk taken from the four quarters, respectively, of the udder of a dairy cow, and wherein the electrical means for generating an electrical signal representative of the conductivity of the sample includes a readout screen providing for the display of four digits; electrical means for comparing a value obtained by said conductivity cell from a test sample of milk taken from one of the four quarters of the udder of a dairy cow, with a reference value and for energizing the display on the readout screen of a digit representative of the resulting comparison value; and switch means for setting said electrical means into respective condition for energizing the display on the readout screen of digits representative of comparison values obtained for respective test samples from the other three quarters of the udder of said dairy cow, while retaining the digit displays already energized.

3. An electrical conductivity testing device in accordance with claim 1, wherein the conductivity cell is removable and may be replaced by a conductivity cell of differing dimensions so as to adjust the device for use with different herd types.

4. An electrical conductivity testing device in accordance with claim 3, wherein the conductivity cell is mounted on a frame and the frame is removable with respect to the device, so that the conductivity cell is replaced by replacing a frame having one conductivity cell mounted thereon with another frame having a different conductivity cell mounted thereon.

5. An electrical conductivity testing device in accordance with claim 1, wherein the electrical means for generating an electrical signal representative of the conductivity of the sample includes a bridge amplifier circuit for sensing electrical impedance deviations of the test sample in the conductivity cell from a reference impedance and for producing resultant electrical signals indicative of the deviation.

6. An electrical conductivity testing device in accordance with claim 5, wherein the electrical means includes means for demodulating and amplifying the resultant electrical signals, an analog to digital converter to which said demodulated and amplified electrical signals are applied, a display readout screen, and a display driver for receiving the output from said converter and providing values representative of said output to be displayed on the readout screen.

7. An electrical conductivity testing device in accordance with claim 5, wherein the bridge amplifier circuit comprises the conductivity cell; a reference resistor, the conductivity cell and reference resistor being connected in electrical parallel; means for applying an alternating current voltage to the parallel connection of the conductivity cell and the reference resistor; a differential operational amplifier, one input of which is electrically connected to the conductivity cell and the other input of which is electrically connected to the reference resistor; a feedback resistor electrically connected between the output of the differential operational amplifier and the input connected to the conductivity cell; and a bias resistor electrically connected between a predetermined voltage and the input of the differential operational amplifier connected to the referenced resistor.

8. An electrical conductivity testing device in accordance with claim 7, wherein the feedback resistor and bias resistor both have substantially the same value of resistance.

9. A method of detecting the presence of mastitis in dairy cows comprising the steps of providing an electrical conductivity testing device for detecting mastitis in dairy cows which device includes reservoir means for receiving spaced, successive samples of milk as squirted directly from a teat of a cow to be tested and of a volume to be at least partially filled by a single squirt of milk, two lengths of electrically conductive tubing, a length of electrically non-conductive tubing joining the lengths of electrically conductive tubing to form an electrical conductivity cell wherein the lengths of electrically conductive tubing form the electrodes of the cell, tubing means in combination with the electrical conductivity cell being included as an integral part of said passage intermediate its ends, said passage being smaller in cross-section than said reservoir means and connected in fluid-flow communication with said reservoir means to form an inlet to said passage, so that milk will flow from said reservoir means into and through said passage, said passage being configured as a loop having its inlet and an outlet above the conductivity testing cell when the device is held in normal testing position, milk to be tested entering the conductivity cell from said reservoir means and remaining there until forced out by the next sample or until otherwise emptied, the said outlet of said passage being located below the said inlet thereof, so that, when a sample of milk reaches equilibrium in said passage, no milk is present in the reservoir or passage inlet, whereby, when a successive sample of milk is received in said reservoir means, an air bubble will be formed in the upper part of said passage between the sample at equilibrium and the successive sample, and the inside diameter of said testing passage being small enough to be effective to maintain any bubbles of air trapped between successive samples as bubbles between such samples and to maintain such bubbles between said samples as the samples flow through the passage to thereby flush the preceeding sample from the conductivity cell, milk discharge means connected in fluid-flow communication with the outlet end of said passage to allow the sample to flow from said passage, and electrical means electrically connected to the respective electrodes of the conductivity cell for generating an electrical signal representative of the conductivity of the sample of milk in the cell at any given time; holding the device under the teat of a diary cow to be tested; squirting milk from a selected teat into the reservoir of said device; allowing the milk to flow from the reservoir into the testing passage until the reservoir is empty; reading the output of the device which serves as an indication of whether mastitis is present; and repeating the procedure with another sample.

10. A method of detecting the presence of mastitis in dairy cows according to claim 9, wherein the output of the device is displayed as a number and if the number is higher than a known minimum value mastitis is indicated as present.

11. A method of detecting the presence of mastitis in dairy cows according to claim 9, wherein the procedure is repeated sequentially for each of the four quarters of the udder of a single cow and a comparison of the readings is made before moving to the next cow.

12. A method of detecting the presence of mastitis in dairy cows according to claim 11, wherein the output of the device is displayed as a number and if the number is higher than a known minimum value for any of the four quarters or if the difference between the lowest and highest number is greater than a known maximum, mastitis is indicated as present.

13. A method of detecting the presence of mastitis in dairy cows according to claim 9, wherein the electrical conductivity testing device includes means for separately reading the conductivity of four successive samples of milk provided to the device; wherein the step of repeating the procedure includes repeating the procedure with milk from each of the four quarters of the udder of a single cow sequentially so that the four successive readings produced by the device will represent readings for each of the four quarters of a single cow; and a comparison of the four readings is made before taking any successive samples.

14. A method of detecting the presence of mastitis in dairy cows according to claim 13, wherein the four readings of the device are displayed as four separate numbers and if a number is higher than a known minimum value for any of the four quarters or if the difference between the lowest and highest number is greater than a known maximum, mastitis is indicated as present.

* * * * *